(12) United States Patent
Lopez (10) Patent No.: US 7,099,731 B2
(45) Date of Patent: Aug. 29, 2006

(54) METHOD OF MANUFACTURING A MULTIPLE COMPONENT DEVICE

(75) Inventor: George A Lopez, Laguna Beach, CA (US)

(73) Assignee: ICU Medical Inc., San Clemente, CA (US)

( * ) Notice: Subject to any disclaimer, the term of this patent is extended or adjusted under 35 U.S.C. 154(b) by 39 days.

(21) Appl. No.: 10/398,432

(22) PCT Filed: Dec. 14, 2000

(86) PCT No.: PCT/US00/34124

§ 371 (c)(1),
(2), (4) Date: Apr. 26, 2004

(87) PCT Pub. No.: WO01/45027

PCT Pub. Date: Jun. 21, 2001

(65) Prior Publication Data

US 2004/0176867 A1 Sep. 9, 2004

Related U.S. Application Data

(60) Provisional application No. 60/170,659, filed on Dec. 14, 1999.

(51) Int. Cl.
*G06F 19/00* (2006.01)

(52) U.S. Cl. .............................. 700/117; 700/95; 705/26
(58) Field of Classification Search ................ 700/117, 700/95–96, 99–101, 106, 107; 705/28, 26, 705/27, 29
See application file for complete search history.

(56) References Cited

U.S. PATENT DOCUMENTS

| 4,900,322 A | | 2/1990 | Adams | |
|---|---|---|---|---|
| 5,009,654 A | * | 4/1991 | Minshall et al. ............ | 604/410 |
| 5,224,049 A | | 6/1993 | Mushabac | |
| 5,359,511 A | | 10/1994 | Schroeder et al. | |
| 5,610,811 A | * | 3/1997 | Honda .......................... | 705/2 |

(Continued)

FOREIGN PATENT DOCUMENTS

| AU | 8930798 A1 | 10/1999 |
|---|---|---|
| FR | 2 768 918 A1 | 2/1999 |
| WO | WO 02/0866797 A1 | 10/2002 |

OTHER PUBLICATIONS

International Search Report.
PCT/US2005/020461, filed Mar. 21, 2002, ICU Medical, Inc.
Fryer, K., Microsoft Press Computer Dictionary, 1997, p. 505, 3$^{rd}$ Edition, Microsoft Press, Redmond, Wa.
http://www.shop.goto.com, 1997–2000, (1 page).
Hernandez, M., Database Design For Mere Mortals, 1997, pp. 46–50, Addison–Wesley Developer Press, U.S.
Castro, E., HTML For The World Wide Web, Visual Quick-start Guide 2$^{nd}$ Edition, 1997 pp. 23, 158–161, Peachpit Press, Berkley, CA.
Rumbaugh, J. et al., Object–Oriented Modeling and Design, 1991, pp.89–91, Prentice–Hall, Inc., Englewood Cliffs, NJ.

(Continued)

*Primary Examiner*—Zoila Cabrera
(74) *Attorney, Agent, or Firm*—Knobbe Martens Olson & Bear LLP (57) ABSTRACT

The present invention is a method of manufacturing a product from at least two individual components comprising the steps of providing data regarding at least a first and a second component to a customer; permitting the customer to request a product comprising the combination of at least the first and the second component; transmitting the request to a first location remote from the customer; receiving at least one of the first and second components at the first location; transporting the first and second components from the first location to a second location; assembling the first and second components into a desired product at the second location; and transporting the assembled product to the customer.

7 Claims, 4 Drawing Sheets

U.S. PATENT DOCUMENTS

| | | | |
|---|---|---|---|
| 5,824,085 A | | 10/1998 | Sahay et al. |
| 5,835,693 A | | 11/1998 | Lynch et al. |
| 5,894,571 A | * | 4/1999 | O'Connor ...................... 713/2 |
| 5,909,023 A | | 6/1999 | Ono et al. |
| 5,963,915 A | | 10/1999 | Kirsch |
| 5,966,697 A | * | 10/1999 | Fergerson et al. ............ 705/26 |
| 5,970,471 A | * | 10/1999 | Hill ............................ 705/26 |
| 6,032,130 A | | 2/2000 | Alloul et al. |
| 6,055,514 A | | 4/2000 | Wren |
| 6,125,353 A | | 9/2000 | Yagasaki |
| 6,131,087 A | | 10/2000 | Luke et al. |
| 6,182,897 B1 | * | 2/2001 | Knowles et al. ....... 235/462.01 |
| 6,236,901 B1 | * | 5/2001 | Goss ........................... 700/95 |
| 6,275,821 B1 | | 8/2001 | Danish et al. |
| 6,304,850 B1 | | 10/2001 | Keller et al. |
| 6,317,722 B1 | * | 11/2001 | Jacobi et al. ................. 705/14 |
| 6,598,223 B1 | * | 7/2003 | Vrhel et al. ................ 717/174 |
| 2001/0042020 A1 | * | 11/2001 | Schachne et al. ............. 705/26 |
| 2002/0091456 A1 | * | 7/2002 | O'Connor .................... 700/97 |
| 2002/0116300 A1 | | 8/2002 | Debusk et al. |
| 2002/0143320 A1 | * | 10/2002 | Levin ............................ 606/1 |

OTHER PUBLICATIONS

G., Object–Oriented Analysis and Design, 1994, pp. 199–203, The Benjamin/Cummings Publishing Company, Inc., U.S.

Brown et al., User Guide to COBOL 2, 1984, pp. 13–16, NCC Publications, England.

Ashley et al., Using Structured COBOL 2, 1984, pp. 308–311, 314–315, 264–266, John Wiley & Sons, Inc., Canada.

Fryer, K., Microsoft Press Computer Dictionary, 1997, pp. 95, 96, 166, 204, 240, 349, 392, 403, 422, 423, 424, 425, 430, 431, 445, 449, 460, 469, $3^{rd}$ Edition, Micrsoft Press, Richmond , WA.

Hane, P., Dialog Launches Internet E–Commerce Strategy, Information Today, Sep. 1998, p. 22, vol. 15, No. 8, United States.

Seachrist, D., Hanging Out An Internet Shingle, BYTE, Apr. 1997, pp. 136–140, vol. 22, No. 4, The McGraw–Hill Companies.

Bruno, L., Dynamic Dividends Dividends, Data Communications, Nov. 1997, pp. 101–104, 106, 108, vol. 26, No. 15, The McGraw–Hill Companies.

Schloss, R.J., Novel Business Uses Of Independently Created Hyperlinks In The World Wide Web: Basic Mechanism and Examples, IEEE, Proceedings of the $29^{th}$ Annual Hawaii International Conference on System Sciences, Jan. 1996, pp. 137–146, vol. 2.

Dunion, T., SingleShop E–Shopping Service Powers iMOM.com, Company Announcement, May 2000, pp. 1–2.

Lowery, J., Buying Online for Dummies, 1998, pp. 73–74, IDG Books Worldwide, Inc., Foster City, Ca.

Website from archive.org: Here's How Peapod Works, Feb. 18, 1998.

Booch, G., Object–Oriented Analysis and Design. 1994, pp. 89–91, Prentice–Hall, Inc., Englewood Cliffs, NJ.

European.

* cited by examiner

METHOD OF MANUFACTURING A MULTIPLE COMPONENT DEVICE

PRIORITY INFORMATION

This application is a National Stage of International Application No. PCT/US2000/34124, filed Dec. 14, 2000, which claims priority to U.S. Provisional Patent Application No. 60/170,659, filed Dec. 14, 1999, both of which are hereby incorporated by reference in their entirety and made part of this specification.

BACKGROUND OF THE INVENTION

1. Field of the Invention

This invention relates generally to methods of manufacturing devices, and specifically to methods of manufacturing devices comprised of multiple component products.

2. Description of the Related Art

Many manufacturers produce a comprehensive line of component products which are designed to interconnect and function together. It is often desirable for such manufacturers to sell their components separately because the varying needs of their customers would not be readily satisfied by any single combination of components, and it is frequently not economically feasible to assemble the components in accordance with the individual needs of every customer at the manufacturing site. In addition, in some industries, manufacturers make individual components which are capable of being used in combination with the components of other manufacturers in the industry.

As a consequence, the customer usually is faced with the inconvenient task of obtaining the desired component parts from one or more manufacturers and then combining them in the desired configuration. When a customer has a continuous need for such a combination of components, the burden of ordering the components and putting them together may become very time-consuming and expensive.

The problem is especially evident in the medical device industry. For example, medical practitioners often require a variety of components to create a desired intravenous (IV) set. The components of an IV set may include IV drip bags, medical tubing, needleless injection sites, Y-sites, luer connectors, etc. Many of these components are repeatedly used together in certain configurations for specific applications at a given hospital or other care center, but the components are generally sold separately by separate manufacturers.

Some medical device manufacturers have permitted their customers to order combinations of such components pre-assembled. However, as described below, the expense and delay heretofore associated with pre-assembled combinations has often been prohibitive, especially in view of the increasing cost constraints placed upon medical practitioners and medical device companies by insurance companies and the consuming public. Thus, despite the recurrent use of a certain combination at a facility, many medical practitioners have still been forced to order the components separately and then assemble them on site.

Figure 1:
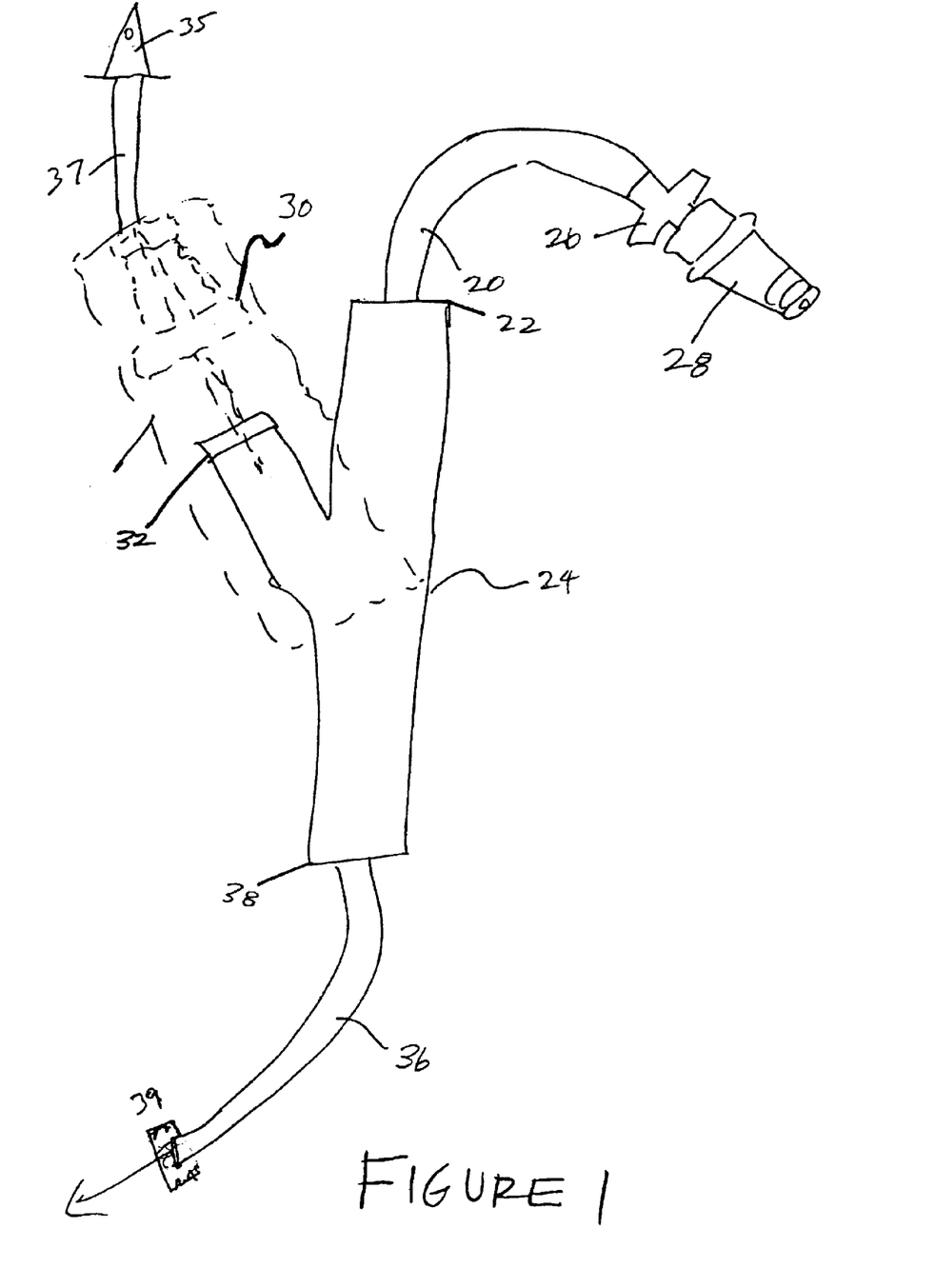
FIG. 1 is a plan view of an example of a combination of medical device component products.

An example of a combination of IV set component parts that might be desired at a given hospital is shown in FIG. 1. In this example, a first end of a section of medical tubing 20 is inserted into a first inlet 22 of a Y-site 24. A female luer 26 and a CLAVE 28 fluid connector (manufactured by ICU Medical, Inc. of San Clemente, Calif.) are attached in series to the opposite end of the medical tubing 20. A PIGGY LOCK connector 30 (also available from ICU Medical, Inc.) is attached to a second inlet 32 of the Y-site 24, and a section of medical tubing 36 is coupled to the outlet port 38 of the Y-site 24. The PIGGY LOCK connector is attached to tubing 37 which is attached to a spike 35. The tubing 36 is connected to a luer lock 39 at its opposite end.

The typical prior art procedure for providing a pre-assembled combination of such an IV set is outlined below. A customer first contacts a manufacturing representative of a company which offers one or more of the components of the desired combination. The manufacturing representative then informs the manufacturer of the request and an employee of the manufacturer must then determine whether the requested combination can be provided in view of applicable governmental regulations.

Assuming the combination is permitted by such regulations, the manufacturing representative then arranges for another employee to put together a sample of the desired combination from the component parts. The sample is then sent to a facility for medical sterilization and packaging, returned from the sterilization facility, and then sent to the customer. In this process, if the manufacturer does not make all of the components of the desired combination, the manufacturer may need to obtain one or more of the components from another manufacturer.

It typically takes about ten days from the time the customer originally requests the sample to the time the customer receives the sample. The customer then evaluates the sample to determine whether it is satisfactory. If the customer approves of the sample, the customer must generally place a minimum bulk order of the combination with the manufacturing representative. In most cases, the customer does not have the option of ordering the desired combination in small quantities.

Bulk orders are usually required because the process of assembling and packaging a specific combination requires reconfiguration of the assembly process and special attention by the manufacturing and distribution personnel, entailing additional expenses which are only compensable by the profits resulting from an order of substantial size.

The assembly process usually takes an extended period of time. After assembly, the products must be sterilized and packaged. The process of sending the products to the sterilization facility, performing the sterilization and packaging, and then sending them back to the manufacturer takes more time. As a consequence of the various delays and inefficiencies, the complete process takes approximately four to six months from the time the customer first contacts the manufacturing representative to the time the customer receives the first bulk order.

Another problem associated with this procedure relates to the end cost of the product. As may be appreciated, the cost of labor is the primary cost associated with producing the product. In this process, a substantial number of man hours are spent in this process preparing the sample product. More man hours, and capital expenditure, are required to produce the minimum order of the product. Because of the substantial man-hours associated with the preparation of the product, the cost of the product is very high. This is especially true when viewed in relation to the number of products produced. This cost is passed on to the consumer, after application of a profit margin by the medical device supplier and hospital. In addition, they often produce several times the amount of the product ordered and keep the remaining product in inventory so that subsequent orders can be filled more quickly.

There is thus a need for an improved method of manufacturing pre-assembled combinations of component parts.

It is an object of the invention to provide a method in which the customer is given more information at the beginning of the ordering process and the assembly process and wherein the assembly and transportation are efficiently controlled in a manner which provides the product more quickly and at a significant reduction in cost.

SUMMARY OF THE INVENTION

The present invention is a method of manufacturing a product from at least two individual components. In general, this method comprises the steps of providing data regarding at least a first and a second component to a customer; permitting said customer to request a product comprising the combination of at least said first and said second component; transmitting said request to a first location remote from said customer; receiving at least one of said first and second components at said first location; transporting said first and second components from said first location to a second location; assembling said first and second components into the desired product at said second location; and transporting said assembled product to said customer.

Preferably, data regarding each individual component and combinations of multiple components is available on a database. The customer accesses this database to determine the availability of particular combinations of components. The database is associated with a program which permits the customer to place an order for an approved combination of components.

In the preferred embodiment, the method is used to create a multi-component medical device, such as an IV set.

DETAILED DESCRIPTION OF THE PREFERRED EMBODIMENT

The present invention overcomes the expense and delay previously associated with providing customers with combinations of component products by using a novel method of bringing all of the components together for assembly, performing the assembly process in an efficient and economical manner, and delivering the assembled components directly to the customer.

Figure 2:
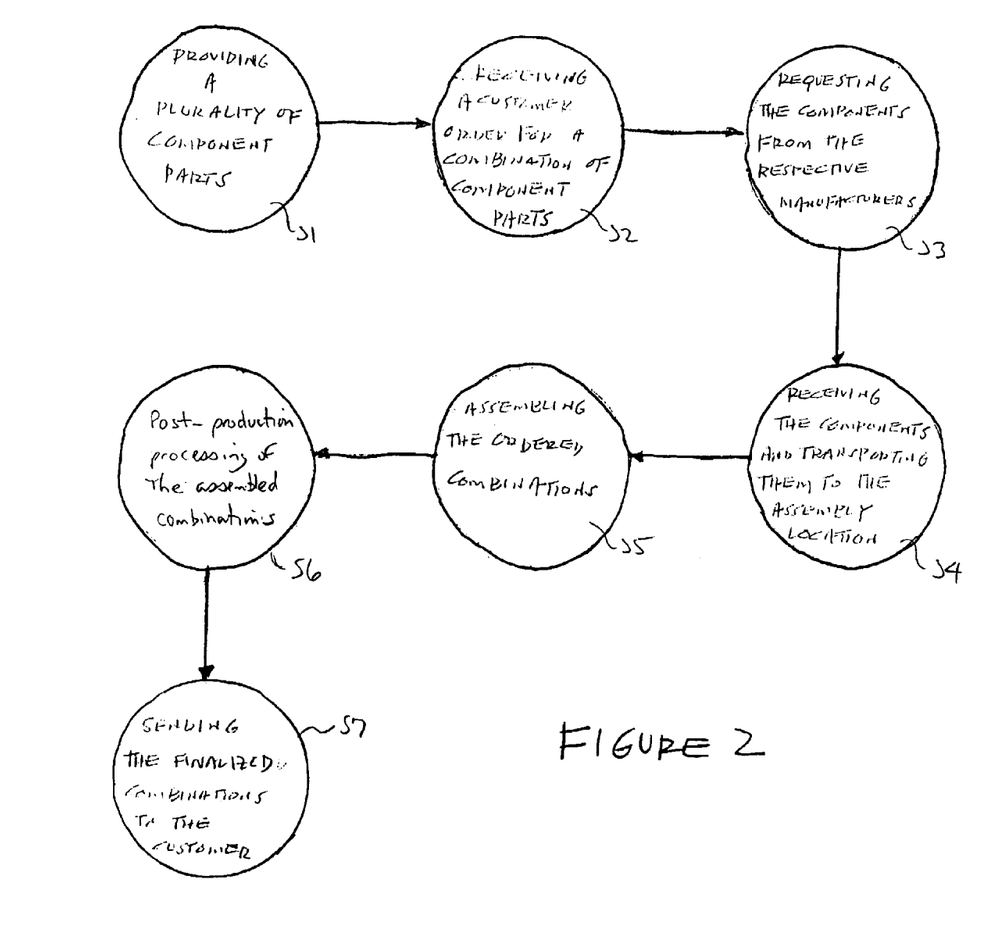
FIG. 2 is a flowchart illustrating the steps of the method of the present invention.

The method of the present invention is broadly illustrated in FIG. 2. In a first step S1, a number of component parts are made generally available to a customer by a vendor. These components may be provided by a number of suppliers or manufacturers. In step S2, a customer places an order with the vendor for a product comprising at least two of the assembled components which are available.

In step S3, the vendor requests each of the assembled components required to produce the combination from the individual suppliers or manufacturers. In step S4, these individual components are delivered to a single location where they are combined in bulk. These unassembled but amassed components are then delivered to an assembly location, where in step S5 they are assembled into the desired combination of the components.

In an optional step S6, the assembled combinations are subjected to post-production processing, such as packaging or sterilization. This processing may take place in a remote location from the location of assembly.

Finally, in step S7, the completed products are shipped directly to the consumer which placed the order in step S2 or an address to which the consumer wishes the products to be delivered.

Figure 3:
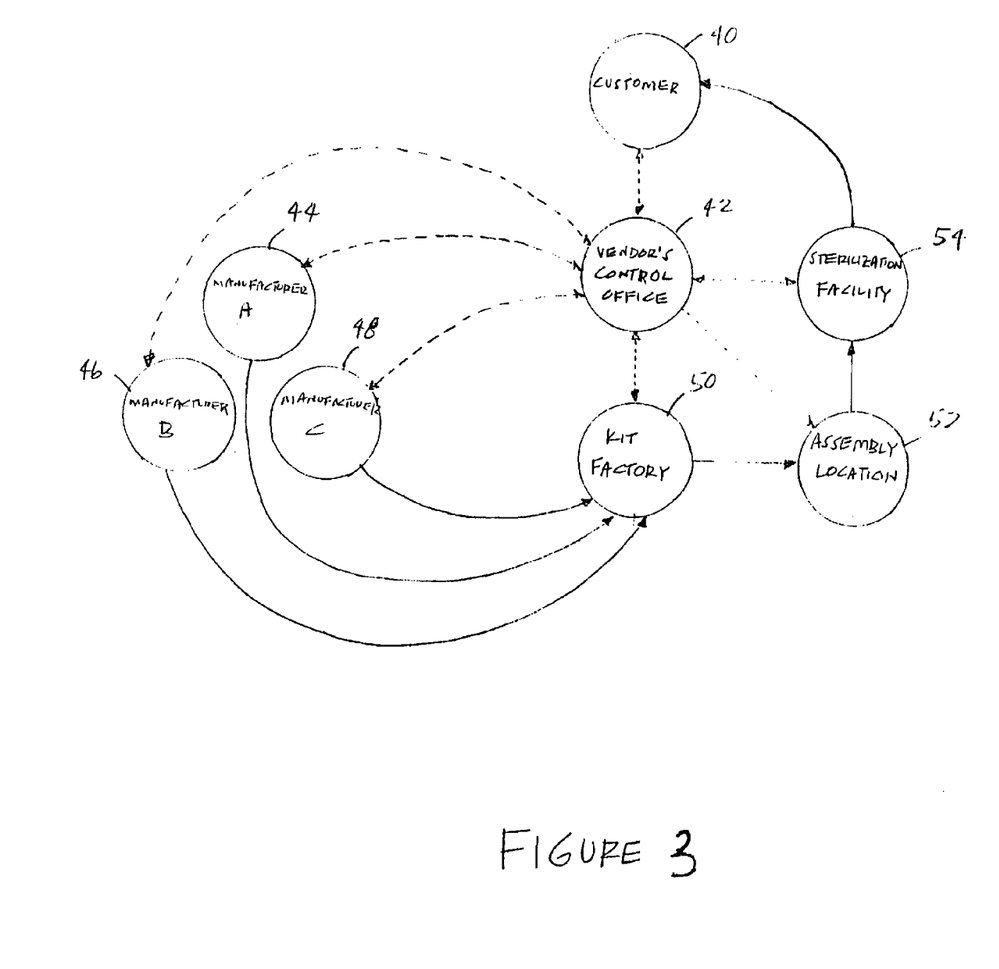
FIG. 3 is a schematic illustrating the interrelationship between the various locations and activities associated with the method of the present invention.

In accordance with the present invention, the method illustrated in flowchart form in FIG. 2 preferably occurs at several locations and involving several parties, the interrelationship of which is illustrated in FIG. 3.

As illustrated in FIG. 3, according to the present invention a vendor preferably provides a customer 40 with means for ascertaining all possible combinations of available components. Preferably, this means provides the customer with information regarding each individual component, as well as combinations thereof. In addition, the customer is provided with information regarding which combinations are prohibited by applicable government regulations.

This means may include a catalog, a telephone system, or preferably, a computer program with a comprehensive database. This database includes information regarding each component, such as the specifications of the component and the like. In the case of a computer database, an illustration of the component is provided on a viewing screen.

A program associated with the database permits the customer to obtain information regarding proposed combinations of individual components. In this arrangement, a customer may utilize a computer at a remote location to access a main computer associated with the vendor which contains the database. The customer's computer communicates with the main computer via the Internet, a telephone link or other means well known in the art. Of course, one or more access computers may be provided at the location of the vendor which the customer may use to obtain the same information. This arrangement is less desirable, however, since the customer must travel to the vendor's location to obtain the information.

Preferably, the program is arranged so that the customer selects individual components from the database and requests their combination. In response, the computer instantly displays the desired combination and indicates whether it is acceptable. For example, in the medical area, the computer database would contain information regarding whether a particular combination of components meets FDA approval.

The means for ascertaining the combination components preferably allows the customer to choose products made by a wide variety of manufacturers. In this way, the customer may, if desired, choose components from different manufacturers to include in the combination. In this arrangement, the database simply includes the necessary information regarding the individual components, regardless of their source, and combinations thereof.

According to a preferred embodiment, once the customer has put together a given combination of products on the computer screen and the computer program has determined that the combination is acceptable, the customer is then permitted to place an order. Preferably, this order is placed directly through the computer which is being used to determine the proposed combinations of components.

When the customer places an order through the main computer, the main computer transmits the customer's order to a control office 42. Depending on the location of the main computer and the control office, this transmission may be through a direct connection, or when the computer and control office are far apart, through an electronic connection such as the Internet or via fax, etc.

As stated above, desirably a computer program forms an integral part of the method, facilitating access to the component and component combination data, as well as permitting ordering.

As one aspect of the invention, a printer or similar device is preferably provided at the kit factory 50 for printing out the order and instructions which are to be provided with the components with are to be assembled at the assembly location 52. The instructions may be arranged to include pre-printed address labels for the assembly location 52 and customer 40 which are used to label the packages to each of these locations.

Most importantly, the method of the present invention permits the customer to order any number of products. Thus, the customer is not required to order a bulk order. As detailed below, the present invention is so efficient that bulk orders are not required to recoup assembly and administrative costs.

The control office 42 is preferably a small, stream-lined facility. There need not be many employees or extensive building space because the fundamental role of the control office is merely to receive electronic orders from the customer, send electronic instructions and receive status reports from other locations involved in the steps of the present invention. In fact, much of the order processing may be carried out by a computer system in the control office without the need for a great deal of employee involvement.

At or after the same time the order placed by the customer is transmitted to the control office 42, a corresponding order is transmitted to each supplier of the components comprising the desired assembled product. The orders which are transmitted to the suppliers or manufacturers of the components may be transmitted with the request to the control office 42, such as in the same or substantially the same step performed by the computer program or other protocol.

Preferably, when the control office 42 receives the customer's order, the control office immediately transmits the order. In the arrangement illustrated, a corresponding request or order is transmitted to three manufacturers 44, 46, 48.

The order is also transmitted to a kit factory 50 associated with the vendors 44, 46, 48. This transmission is also preferably via a computer network.

The manufacturers' 44, 46, 48 involvement may be limited to just receiving orders and sending individual components, a task to which they are already well adapted. In that regard, the orders transmitted thereto are preferably for the manufacturer to deliver or transport the desired components to the kit factory 50.

In this arrangement, the kit factory 50 is a facility which desirably has very little storage capacity for component parts. The reduction in total inventory contributes to a lower cost of production.

Instead, the kit factory 50 simply serves as a location where orders are received and to which component parts from the manufacturers are amassed and then sent to an assembly location. As a result, the kit factory operates as economically as possible.

In a preferred arrangement, the kit factory 50 has some inventory, permitting immediate amassing of the necessary parts for forwarding to the assembly location 52. In this arrangement, the orders are placed with the manufacturers 46, 48, 50 to provide immediate replacement of the depleted minimal inventory.

The respective manufacturers 44, 46, 48 transport their requested components to the kit factory 50. The components may be transported by truck, airplane or any means known to those of skill in the art.

The components arrive at the kit factory a short time, preferably the same day or within a few days, after the customer's order is first received. In that event, if insufficient inventory existed, the time to receive additional components is minimal, and used inventory is immediately replenished. To reduce the cost associated with transportation, the kit factory 50 is desirably located close to the manufacturers 44, 46, 48, but also close to an assembly location 52, described below.

An employee at the kit factory 50 then rapidly amasses the separate components from the manufacturers together with assembly instructions regarding how the components are to be combined. In a preferred embodiment, the description consists of a simplified schematic picture generated by the computer system of the combined components. The picture is desirably included in the package containing the separate components and the package is then sent to the assembly location 52. The picture or other instructions may contain a bar code which is read at each step of the process so that the computer will record exactly where any particular order is. A customer may be given access to the bar code system to "track" the progress of the customer's orders.

Of course, in alternative embodiments, any of the locations where the method steps are performed may be combined, or the locations may be very close to each other, such as different rooms in the same building.

In order to further limit the total cost of producing the desired combination of component products, the assembly location 52 is preferably situated in a place where labor costs are substantially lower, such as a foreign country (such as Mexico), thereby significantly diminishing the cost of assembly. The components are quickly combined into the desired combinations by the personnel at the assembly location 52 with reference to the schematic picture or other assembly instructions which are conveniently provided along with the bulk components.

After assembly, the products may be sent to a post-production location 54. In the case of medical devices, this location comprises a sterilization and packaging facility. In that arrangement, the assembled combinations are therefore sent from the assembly location 52 to a sterilization plant 54. After sterilization and packaging, the products are then preferably sent directly to the customer 40. Alternatively, the products may be sent to a hub which then distributes the products to customers, as will be understood by those of skill in the art.

In the preferred embodiment, the method of manufacture is utilized to create medical devices from individual components. An example of the method as utilized to create a medical device will be described with reference to FIGS. 1 and 4.

A customer is interested in obtaining the assembled product illustrated in FIG. 1 and described above. The customer accesses the vendor's main computer containing the above-referenced database. The customer locates each of the individual components of the product in the database. In this case, the components include a standard CLAVE connector 28, tubing 20, Y-site 24, adapter 26 and PIGGY LOCK® connector 30. (The remaining components shown in FIG. 1 will not be described for simplicity.)

Figure 4:
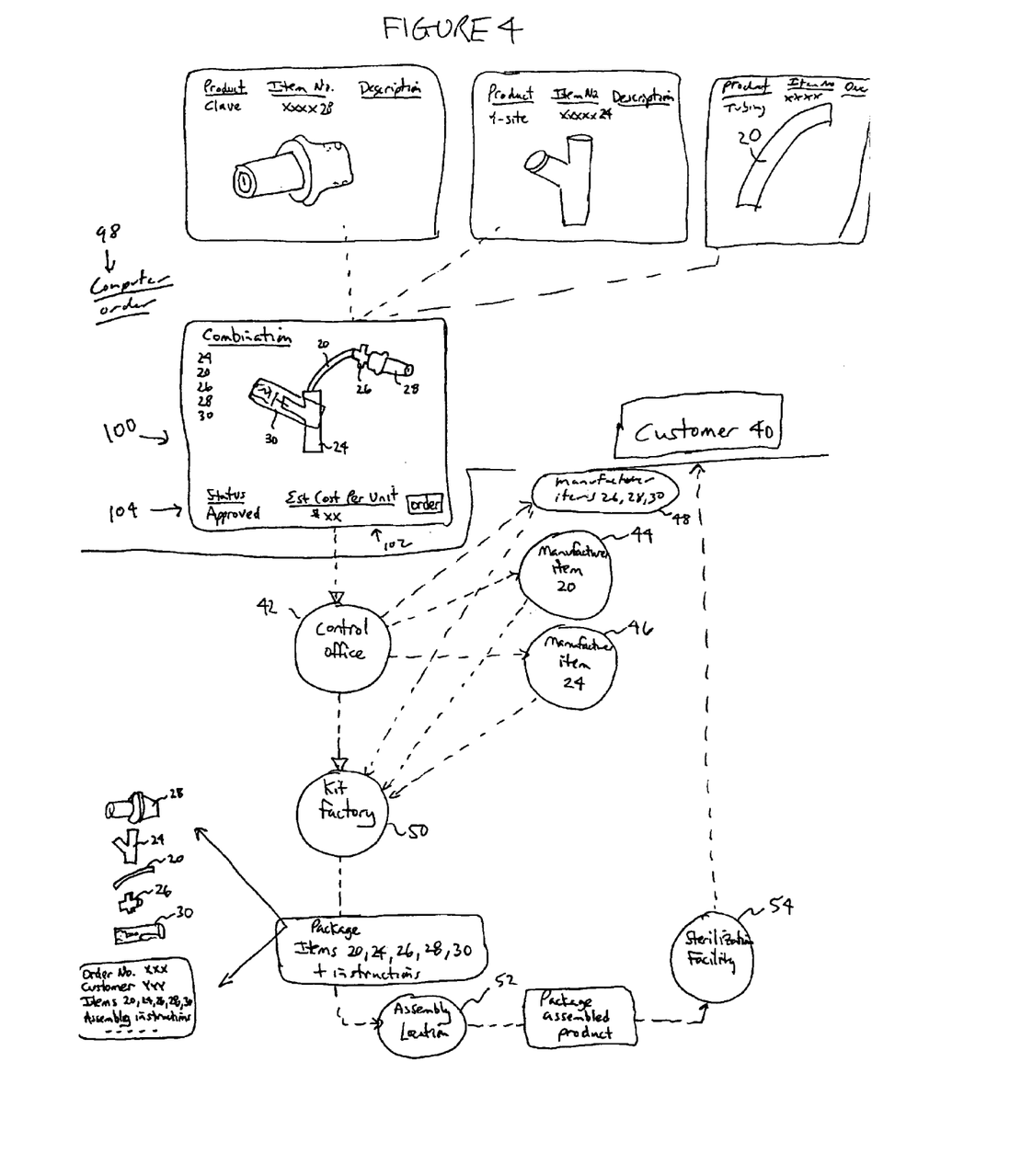
FIG. 4 is a schematic illustrating the method of the present invention as used to create the product illustrated in FIG. 1.

The customer instructs the main computer to create a "cyber" version of these components assembled into the desired product configuration 98. This product configuration is illustrated on the screen of the customer, as illustrated in FIG. 4 at 100. The screen preferably displays data regarding the cost per unit of the product 102 and whether the combination can be produced in light of governing regulations 104.

If the combination is approved, the customer orders a quantity of the product. This order is received at the control office 42. Either simultaneous with the customer's order, or at or near the time of receipt thereof at the control office 42, an order is sent to the manufacturer or supplier of each of the individual components, requesting their delivery to the kit factory 50.

Upon receipt of the individual components, an employee at the kit factory 50 prepares a package containing the raw materials, i.e. components, necessary for assembly of the final product. In this case, if 100 of the product illustrated on the customer's computer screen have been ordered, at least 100 of each of items 20, 24, 26, 28 and 30 are placed into the package. In addition, an instruction and data sheet is provided with this package. This sheet preferably contains data regarding the order, the customer and how the individual components are to be assembled to complete the combination. The assembly instructions preferably include a pictorial representation of the assembled product which may be used as a guide in the assembly process.

This package is delivered to the assembly location 52. At this location, the instructions are utilized to assemble the completed product from the individual components. The assembled products are then placed into a package and delivered to the sterilization facility 54. At this facility, each product is sterilized and/or packaged. The products are then delivered to the customer 40 or a distribution hub.

Many advantages are realized using the above-described invention. First, the method of the present invention provides products to customers much faster than conventional methods. In fact, customers may receive the products ordered in a few days as opposed to weeks or months later. In addition, the cost to manufacture the products is dramatically reduced. Samples do not need to be produced, and inventory is kept to a minimum as described above.

The above is a description of the application of the method of the present invention to a single product. Those of skill in the art will appreciate how the method may be applied to create a wide range of products from individual components.

Of course, the foregoing description is that of preferred embodiments of the invention, and various changes and modifications may be made without departing from the spirit and scope of the invention, as defined by the appended claims.

What is claimed is:

1. A computer-based method of manufacturing a medical product from at least two individual components comprising the steps of:

providing data from a computer database regarding at least a first and a second component to a customer, wherein the data includes an illustration of at least two components on a viewing screen;

permitting said customer to request a product comprising the combination of at least said first and second components;

determining whether the requested combination complies with at least one government regulation:

electronically transmitting information about the requested combination to a first location remote from said customer;

receiving at least one of said first and second components at said first location;

transporting said first and second components from said first location to a second location;

assembling said first and second components into the desired product using the electronically transmitted information at said second location; and transporting said assembled product to said customer.

2. The method in accordance with claim 1, further comprising the step of simultaneously transmitting a request to a supplier of said first and or second component at the same time as said request is transmitted to said first location, requesting transport of said first and/or second component to said first location.

3. The method in accordance with claim 1, wherein said components are medical device components.

4. The method in accordance with claim 1, further including the step of transporting said assembled product from said second location to a third location and sterilizing said product at said third location.

5. The method in accordance with claim 1, further including the step of packaging said assembled product.

6. A medical product comprising at least one first and one second component, said product produced by: providing a computer database containing information regarding combinations of at least a first and a second component, accessing said computer database to determine the availability of a particular combination of components, obtaining data from said database regarding first and second components, including an illustration of said first and second components, determining whether said combination complies with at least one government regulation, placing an order for said combination, electronically transmitting said order to a first remote location, transmitting an order for each component to a supplier of that component, transporting said component to said first remote location, amassing said components at said first remote location, transporting said components to a second location, assembling said components into said combination, and transporting said combination to a destination.

7. The product in accordance with claim 6, further including the step of sterilizing said combination of assembled components.

* * * * *

UNITED STATES PATENT AND TRADEMARK OFFICE
CERTIFICATE OF CORRECTION

| | |
|---|---|
| PATENT NO. | : 7,099,731 B2 |
| APPLICATION NO. | : 10/398432 |
| DATED | : August 29, 2006 |
| INVENTOR(S) | : George A. Lopez |

It is certified that error appears in the above-identified patent and that said Letters Patent is hereby corrected as shown below:

On the Title Page, Column 2 (Foreign Patent Documents), Line 3, delete "02/0866797" and insert -- 02/086797 --, therefor.

On the Title Page, Column 2 (Other Publications), Line 2, delete "2002," and insert -- 2006, --, therefor.

On the Title Page, Column 2 (Other Publications), Line 6, delete "http://www.shop.goto.com," and insert -- [http://www.shop.goto.com] --, therefor.

On the Title Page, Column 2 (Other Publications), Line 11, delete "Berkley," and insert -- Berkeley, --, therefore.

On the Title Page, Column 2 (Other Publications), Line 13, delete "pp.89-91," and insert -- pp. 89-91, --, therefor.

On Page 2, Column 1 (Other Publications), Line 1, before "G.," insert -- Booch, --.

On Page 2, Column 1 (Other Publications), Line 4, delete "2, 1984," and insert -- 85, 1985, --, therefor.

On Page 2, Column 2 (Other Publications), Line 3, delete "Micrsoft" and insert -- Microsoft --, therefor.

On Page 2, Column 2 (Other Publications), Line 4, delete "Richmond ," and insert -- Redmond, --, therefor.

On Page 2, Column 2 (Other Publications), Line 11, after "Dividends" delete "Dividends".

UNITED STATES PATENT AND TRADEMARK OFFICE
CERTIFICATE OF CORRECTION

PATENT NO. : 7,099,731 B2  
APPLICATION NO. : 10/398432  
DATED : August 29, 2006  
INVENTOR(S) : George A. Lopez It is certified that error appears in the above-identified patent and that said Letters Patent is hereby corrected as shown below:

On Page 2, Column 2 (Other Publications), Line 27, delete "European." and insert -- European Patent Office, European Search Report issued in Application No. EP 00 98 4456 on March 11, 2005. --, therefor.

In Column 1, Line 64, delete "CLAVE" and insert -- CLAVE® --, therefor.

In Column 1, Line 67, delete "LOCK" and insert -- LOCK® --, therefor.

In Column 2, Line 3, delete "LOCK" and insert -- LOCK® --, therefor.

In Column 6, Line 64, delete "CLAVE" and insert -- CLAVE® --, therefor.

In Column 8, Line 9 (approx.), in Claim 1, delete "regulation:" and insert

-- regulation; --, therefor.

Signed and Sealed this

Eleventh Day of September, 2007

JON W. DUDAS  
*Director of the United States Patent and Trademark Office*